(12) United States Patent
Sharma et al.

(10) Patent No.: US 11,051,780 B2
(45) Date of Patent: Jul. 6, 2021

(54) AUTOMATICALLY GENERATING SYNCHRONIZED VIEW AND LEVEL OF CONCORDANCE OF DIAGNOSTIC EXAMS

(71) Applicant: Siemens Healthcare GmbH, Erlangen (DE)

(72) Inventors: Puneet Sharma, Princeton Junction, NJ (US); Ulrich Hartung, Langensendelbach (DE); Chris Schwemmer, Forchheim (DE); Ruth J. Soenius, New York, NY (US); Dominik Neumann, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 325 days.

(21) Appl. No.: 16/218,646

(22) Filed: Dec. 13, 2018

(65) Prior Publication Data

US 2020/0029926 A1 Jan. 30, 2020

Related U.S. Application Data

(60) Provisional application No. 62/703,173, filed on Jul. 25, 2018.

(51) Int. Cl.
*A61B 6/00* (2006.01)
*G06T 7/00* (2017.01)
(Continued)

(52) U.S. Cl.
CPC ............ *A61B 6/5229* (2013.01); *A61B 6/032* (2013.01); *A61B 6/037* (2013.01); *G06T 7/0012* (2013.01);
(Continued)

(58) Field of Classification Search
CPC ....... A61B 6/5229; A61B 6/037; A61B 6/032; A61B 5/055; A61B 6/5217; A61B 6/463;
(Continued)

(56) References Cited

U.S. PATENT DOCUMENTS

2011/0235898 A1* 9/2011 Watanabe ................. G06T 7/33
382/154
2019/0237184 A1 8/2019 Sharma et al.

FOREIGN PATENT DOCUMENTS

| CN | 101233521 A | * | 7/2008 | ............... A61B 6/08 |
| CN | 108523931 A | * | 9/2018 | ........... A61B 8/5207 |
| EP | 3518245 A1 | | 7/2019 | |

OTHER PUBLICATIONS

Ortiz-Pérez José T. et al.: "Correspondence Between the 17-Segment Model and Coronary Arterial Anatomy Using Contrast-Enhanced Cardiac Magnetic Resonance Imaging", JACC: Cardiovascular Imaging, vol. 1, Issue 3, May 2008, pp. 282-293.
(Continued)

*Primary Examiner* — Amandeep Saini
(74) *Attorney, Agent, or Firm* — Harness, Dickey & Pierce, P.L.C.

(57) ABSTRACT

An embodiment of a method includes providing a first result list indicating a plurality of first anatomic structures and indicating, for each respective first anatomic structure of the plurality of first anatomic structures, a corresponding first severity indicator; providing a second result list indicating, for each respective second anatomic structure of the plurality of the second anatomic structures, a corresponding second severity indicator; providing a relationship matrix indicating a level of interrelatedness between the first anatomic structures and the second anatomic structures; and generating, based on the first result list provided, on the second result list and on the relationship matrix provided, a concordance visualization indicating a respective level of
(Continued)

concordance between at least one of the first anatomic structures and the corresponding first severity indicator, and indicating a respective level of concordance between at least one of the second anatomic structures and the corresponding second severity indicator.

20 Claims, 5 Drawing Sheets

(51) Int. Cl.
*A61B 6/03* (2006.01)
*G06T 7/174* (2017.01)
*G16H 30/40* (2018.01)
*G16H 30/00* (2018.01)
*A61B 5/055* (2006.01)
*G16H 50/20* (2018.01)

(52) U.S. Cl.
CPC ............. *G06T 7/174* (2017.01); *G16H 30/40* (2018.01); *A61B 5/055* (2013.01); *G06T 2207/10081* (2013.01); *G06T 2207/10104* (2013.01); *G06T 2207/10108* (2013.01); *G06T 2207/30004* (2013.01); *G06T 2210/41* (2013.01); *G16H 30/00* (2018.01); *G16H 50/20* (2018.01)

(58) Field of Classification Search
CPC ....... A61B 6/5235; A61B 6/507; A61B 6/503; A61B 6/504; G16H 30/40; G16H 30/00; G16H 50/20; G06T 7/174; G06T 7/0012; G06T 2210/41; G06T 2207/10104; G06T 2207/30004; G06T 2207/10081; G06T 2207/10108
USPC ........................................................ 382/128
See application file for complete search history.

(56) References Cited

OTHER PUBLICATIONS

Raff G. L. Et. Al., "SCCT guidelines for the interpretation and reporting of coronary computed tomographic angiography.", Journal of Car-diovascular Computed Tomography 3, pp. 122-136, 2009.

* cited by examiner

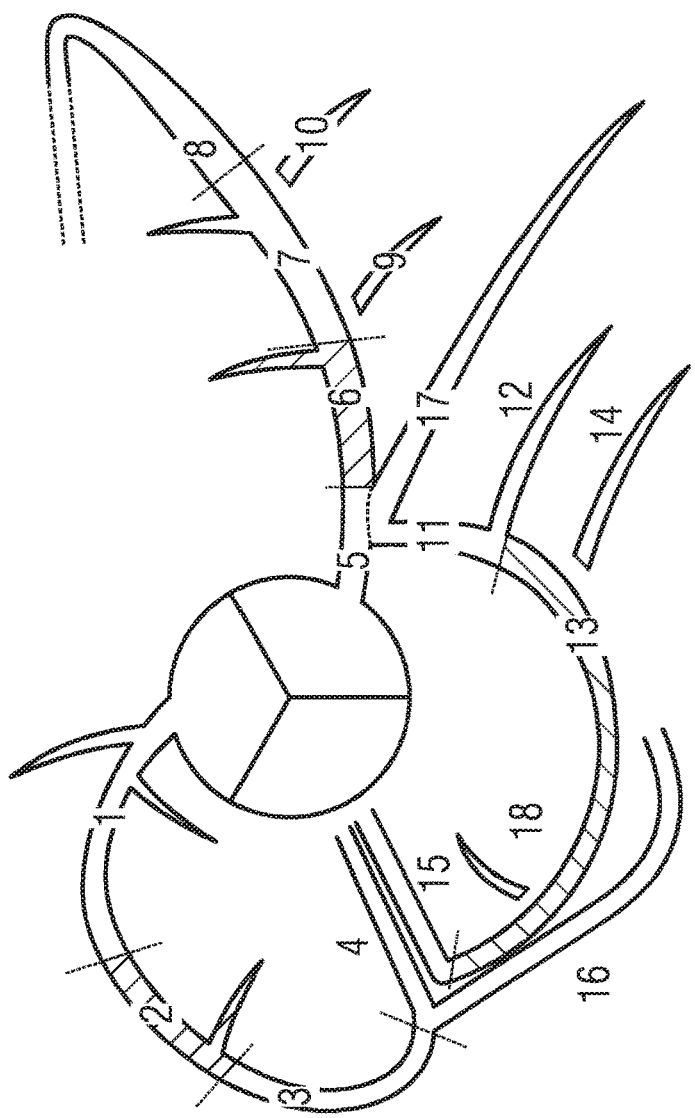
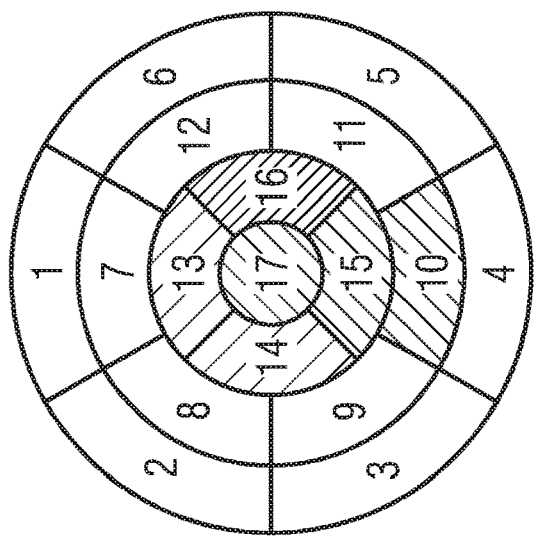
FIG 4

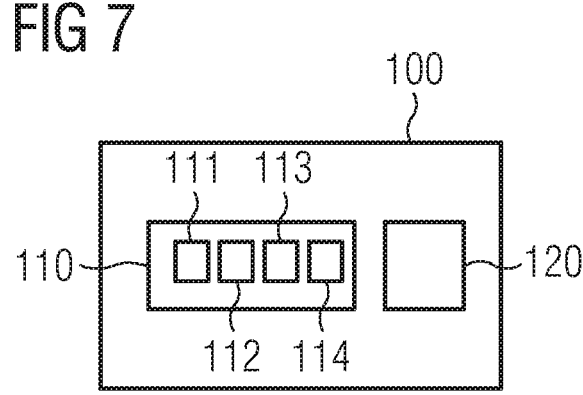
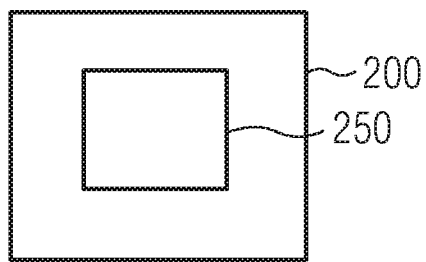 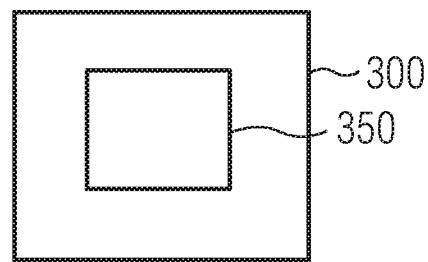

AUTOMATICALLY GENERATING SYNCHRONIZED VIEW AND LEVEL OF CONCORDANCE OF DIAGNOSTIC EXAMS

PRIORITY STATEMENT

The present application hereby claims priority under 35 U.S.C. § 119(a) to U.S. Provisional Patent Application Ser. No. 62/703,173 filed Jul. 25, 2018, the entire contents of which are hereby incorporated herein by reference.

FIELD

Embodiments of the invention generally relate to a method and a system for analyzing medical imaging results, in particular for aiding a physician or a clinician to detect, verify or corroborate a concordance between results of different modalities. In particular, at least one embodiment of the method relates to automatically generating a synchronized view and a level of concordance of diagnostic exams, specifically applied to coronary artery diseases.

BACKGROUND

Nowadays, a large variety of different imaging exams for diagnosing conditions of patients are available from a large number of different modalities. Among these imaging exams are so-called anatomical imaging exams (or: morphological imaging exams or structural imaging exams) and functional imaging exams (or: physiological imaging exams).

Functional imaging is a medical imaging technique of detecting or measuring changes in a metabolism, blood flow, regional chemical composition, adsorption, and/or the like. In contrast to anatomical imaging (or: structural imaging), functional imaging centers on determining physiological activities within a certain tissue or organ by employing medical imaging modalities that, for example, use tracers or probes to reflect spatial distribution of the activities within the body.

By contrast, anatomical imaging, or a structural imaging, provides information about the present anatomical structures of interest within the patient.

Often, a complete medical diagnosis is facilitated, or even enabled, by comparing results from different imaging exams, in particular from the modalities, and determining a level of concordance between the different results.

For example, in the diagnosis of coronary artery disease (CAD) often multiple imaging exams are required, each with its own set of interpretation and findings, often providing complementary information. These findings are documented in radiology and/or cardiology exam reports. Given the heterogeneity of reporting guidelines for each imaging technique, it is not easy to correlate the findings from the various exams in a comprehensive manner which is a task increasingly required for clinical decision reports.

In the prior art, the clinician typically uses data from different exams and individually puts it in context of their clinical experience and knowledge to take a decision or make a recommendation. Concordances between results from different exams, in particular from different modalities, are however very complicated and may require the clinician to rely, to some degree, on their "gut feeling".

For example, currently the concordance level between an anatomical finding and a functional finding is made by a comparison of available results and an assessment of the results performed by e.g. a cardiologist in the case of exams of a human heart. This is mainly done by reviewing the results of, for example, a computed tomography angiography CTA where there is a clear evidence of a, for example, mid-to-severe stenosis within a mid segment of the left anterior descending artery.

The question for the cardiologist is then whether this is relevant finding with the necessity to treat exactly this location or not.

In order to answer this question, a functional assessment may be necessary or helpful. In this case, for instance a stress-perfusion echocardiography is performed. The result of this examination may show that there is a stress-induced decreased blood perfusion at an induced heart rate of e.g. 135 per minute.

The blood perfusion within the mid anterior to anteroapical segment of the heart may be decreased, whereas at rest (heart rate e.g. 65 per minute) there is regular blood flow. Based on the computed tomographic angiography, the anatomy may show that there are no other vessels near this heart segment (mid anterior to anteroapical) and thus the conclusion is drawn by the physician that these findings are related to each other based on their experience.

In another case, only a mild stenosis may be visible in a computed tomographic angiography CTA examination within the proximal part of the right coronary artery but the functional stress test imaging exam based e.g. on SPECT may show a blood perfusion deficit visible within the inferior wall. This may then be interpreted by the cardiologist with a false positive result out of the SPECT examination since the computed tomographic angiography CTA shows only a mild stenosis. In other words, the cardiologist may determine there to be a low level of concordance.

A third example is a clear mismatch of findings like a medium to severe stenosis in the middle of the right coronary artery from an anatomical imaging exam combined with a perfusion deficit in the basal anteroseptal heart segment from a functional imaging exam. Again, in this case a low level of concordance is to be determined.

Some terminology and methodology in the field of computed tomographic angiography, CTA, are known e.g. from the scientific publication by Gilbert L. Raff et al.: "Guidelines; SCCT guidelines for the interpretation and reporting of coronary computed tomographic angiography", Journal of Cardiovascular Computed Tomography (2009) 3, 122-136, Society of Cardiovascular Computed Tomography, 2400 N Street NW, Washington, D.C. 20037, USA; obtainable e.g. from the URL https://secardiologia.es/images/grupostrabajo/cardiorm-cardiotc/guias/interpretation-ccta-2009-scct.pdf, hereafter also cited as "Raff et al.", the entire contents of each of which are hereby incorporated herein by reference.

Some terminology and methodology in the field of perfusion imaging as well as correlations between functional and anatomical imaging exams are known e.g. from the scientific publication by Jose T. Ortiz-Perez et al.: "Correspondence Between the 17-Segment Model and Coronary Arterial Anatomy Using Contrast-Enhanced Cardiac Magnetic Resonance Imaging", JACC: Cardiovascular Imaging, Volume 1, Issue 3, May 2008, Pages 282-293, hereafter also cited as "Ortiz-Perez et al.", the entire contents of each of which are hereby incorporated herein by reference.

A more sophisticated approach is by employing advance image processing algorithms such as image fusion and image registration to fuse two or more images from different exams, in particular from different modalities.

SUMMARY

The inventors have discovered that a drawback of the image fusion approach is that it requires access to advanced post-processing workstations and/or 3D labs which are not common and are therefore expensive or require considerable waiting time. In addition, the inventors have discovered that this approach requires the availability of all of the imaging exams in one location which is not usually the case when the exams are performed, for example, at different facilities.

Embodiments of the present invention are directed to providing a method and/or a system for analyzing medical imaging results in order to support a clinician or physician with a diagnostic task for which results from different medical imaging exams, in particular from different modalities, are available.

According to a first embodiment of the present invention, a computer-implemented method for analyzing medical imaging results is provided, the computer-implemented method including:

providing a first result list of a first type of medical imaging exam of a patient, wherein the first result list indicates a plurality of first anatomic structures and for each of the first anatomic structures a corresponding first severity indicator;

providing a second result list of a second type of medical imaging exam of the patient, wherein the second result list indicates a plurality of second anatomic structures and for each of the second anatomic structures a corresponding second severity indicator;

providing a relationship matrix indicating a level of interrelation (or interrelatedness) between the first anatomic structures and the second anatomic structures; and generating, based on the provided first result list, the provided second result list and the provided relationship matrix, a concordance visualization indicating a respective level of concordance between at least one of the first anatomic structures and the corresponding first severity indicator on the one hand, and at least one of the second anatomic structures and the corresponding second severity indicator on the other hand.

According to a second embodiment of the present invention, a system for analyzing medical results is provided, the system comprising at least one processor configured to perform the method according to an embodiment of the present invention and a display device configured to display the generated concordance visualization.

According to a second embodiment of the present invention, a system for analyzing medical results, comprises:

at least one processor configured to provide a first result list of a first type of medical imaging exam of a patient, the first result list indicating a plurality of first anatomic structures and indicating, for each respective first anatomic structure of the plurality of first anatomic structures, a corresponding first severity indicator, provide a second result list of a second type of medical imaging exam of the patient, the second result list indicates a plurality of second anatomic structures and indicating, for each respective second anatomic structure of the plurality of the second anatomic structures, a corresponding second severity indicator, provide a relationship matrix indicating a level of interrelatedness between the first anatomic structures and the second anatomic structures, and generate, based on the first result list provided, on the second result list and on the relationship matrix provided, a concordance visualization indicating a respective level of concordance between at least one of the first anatomic structures and the corresponding first severity indicator, and indicating a respective level of concordance between at least one of the second anatomic structures and the corresponding second severity indicator; and a display device configured to display the concordance visualization generated.

According to a third embodiment of the present invention, a computer program product is provided which comprises executable program code configured to, when executed by a processor, perform the method according to an embodiment of the present invention.

According to a fourth embodiment of the present invention, a non-transitory computer-readable data storage medium is provided which comprises executable program code configured to, when executed by a processor, perform the method according to an embodiment of the present invention.

According to a fifth embodiment of the present invention, a data stream is provided which comprises, or is configured to generate, executable program code configured to, when executed by a processor, perform the method according to an embodiment of the present invention.

Additional advantages, beneficial options and variance are provided by the claims and the following description with reference to the figures.

The invention will be explained in greater detail with reference to example embodiments depicted in the drawings is appended.

BRIEF DESCRIPTION OF THE DRAWINGS

The accompanying drawings are included to provide a further understanding of the present invention and are incorporated in and constitute a part of this specification. The drawings illustrate the embodiments of the present invention and together with the description serve to explain the principles of the invention.

Other embodiments of the present invention and many of the intended advantages of the present invention will be readily appreciated as they become better understood by reference to the following detailed description.

FIG. 4 shows one possible type of graphical concordance visualization;

FIG. 7 shows a schematic block diagram illustrating a system according to a second embodiment of the present invention;

FIG. 8 shows a schematic block diagram illustrating a computer program product according to a third embodiment of the present invention; and FIG. 9 shows a schematic block diagram illustrating a data storage medium according to a fourth embodiment of the present invention.

Figure 1:
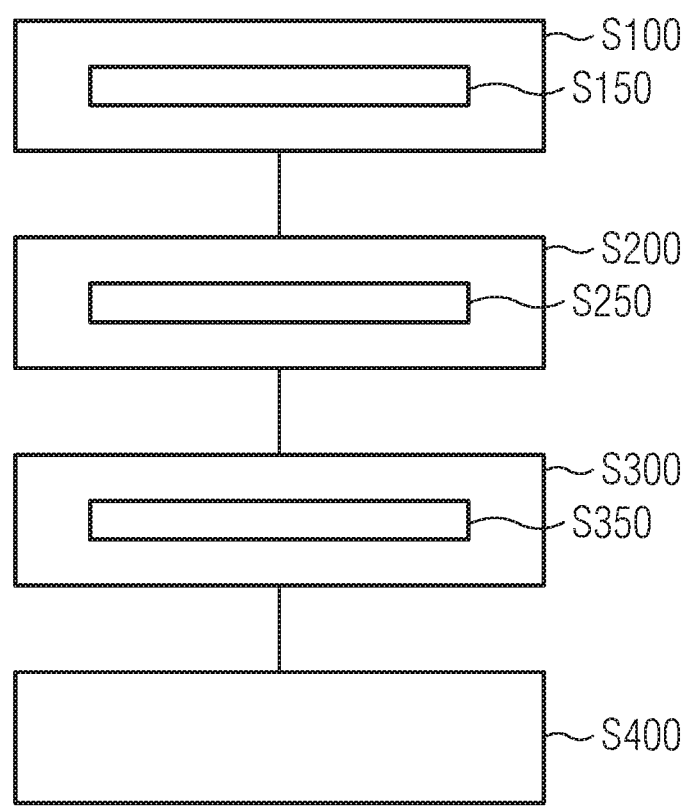
FIG. 1 schematically illustrates a flow diagram for illustrating a computer-implemented method for analyzing medical imaging results according to a first embodiment of the present invention.

The numbering of method steps does not, unless specifically described otherwise, imply that the steps have to be performed in the order of their numbering. In particular, several steps may be performed simultaneously.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Bluray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

According to a first embodiment of the present invention, a computer-implemented method for analyzing medical imaging results is provided, the computer-implemented method including:

providing a first result list of a first type of medical imaging exam of a patient, wherein the first result list indicates a plurality of first anatomic structures and for each of the first anatomic structures a corresponding first severity indicator;

providing a second result list of a second type of medical imaging exam of the patient, wherein the second result list indicates a plurality of second anatomic structures and for each of the second anatomic structures a corresponding second severity indicator;

providing a relationship matrix indicating a level of interrelation (or interrelatedness) between the first anatomic structures and the second anatomic structures; and generating, based on the provided first result list, the provided second result list and the provided relationship matrix, a concordance visualization indicating a respective level of concordance between at least one of the first anatomic structures and the corresponding first severity indicator on the one hand, and at least one of the second anatomic structures and the corresponding second severity indicator on the other hand.

Preferably, the first type of medical imaging exam is a medical imaging exam performed by a first modality, and the second type of medical exam is performed by a second modality, wherein the first and the second modalities are different.

A severity indicator shall be understood to mean an indicator that indicates in some way a severity, likelihood, strength, acuteness and/or the like of a medical or anatomical condition, situation, physiological activity and/or the like. For example, a severity indicator may indicate a severity of a stenosis in a particular blood vessel in a computed tomography angiographic exam, a strength of perfusion in a single proton emission computed tomography (SPECT) exam or the like.

The first or second severity indicator may be a single number or may comprise a tensor (such as a metrics or a vector) of values which may be processed, or used in a calculation, for determining a single severity value.

A level of interrelation (or interrelatedness) is supposed to be understood as comprising a known relationship, in particular a causal relationship, between anatomic structures or between an anatomic structure on the one hand and a physiological activity on the other hand, between two physiological activities and/or the like. For example, a stenosis in specific coronary artery segments may be known to be associated with a perfusion in specific segments.

In some instances, for some types of medical exams and/or for some anatomic structures, the interrelatedness may simply encode that one or more anatomic structures for which results are determined by the first type of medical imaging exam are divided into one or more different anatomic structures for which results are provided by a second type of medical imaging exam, for example due to historic or practical reasons.

The relationship matrix may then indicate the interrelatedness, or even identity, of some of the plurality of first anatomic structures with some of the plurality of second anatomic structures.

Generating the concordance visualization, which may be output by a display device for example, greatly enhances the ability of a physician or a clinician to quickly determine whether the first and the second result lists corroborate a diagnosis, for example when there is a high concordance level indicated by the concordance visualization between at least one result of the first result list and at least one result of the second result list or whether the first and the second result lists provide contradictory or conflicting information.

According to a second embodiment of the present invention, a system for analyzing medical results is provided, the system comprising at least one processor configured to perform the method according to an embodiment of the present invention and a display device configured to display the generated concordance visualization.

The computing device may be realised as any device for computing, in particular for executing a software, an app, or an algorithm. For example, the computing device may comprise at least one processor including at least a central processing unit (CPU) and a memory operatively connected to the CPU. The computing device may also comprise an array of CPUs, an array of graphical processing units (GPUs), at least one application-specific integrated circuit (ASIC), at least one field-programmable gate array, or any combination of the foregoing. The computing device comprises an output interface for outputting signals, for example to the display device, and an input interface for receiving data (e.g. information about at least one patient).

The display device may be a monitor, a computer screen, a touch screen, a holographic screen, a virtual reality display, an augmented reality display, a mixed reality display and/or the like.

According to a third embodiment of the present invention, a computer program product is provided which comprises executable program code configured to, when executed by a processor, perform the method according to an embodiment of the present invention.

According to a fourth embodiment of the present invention, a non-transitory computer-readable data storage medium is provided which comprises executable program code configured to, when executed by a processor, perform the method according to an embodiment of the present invention.

According to a fifth embodiment of the present invention, a data stream is provided which comprises, or is configured to generate, executable program code configured to, when executed by a processor, perform the method according to an embodiment of the present invention.

In some advantageous embodiments, the first type of medical imaging exam is an anatomical imaging exam and/or the second type of medical imaging exam is a functional imaging exam. In this way, the individual strength of both types of imaging exams may be combined, eliminating or obviating possible weaknesses or limitations of either of the imaging exams.

Examples of anatomical imaging include computed tomography (CT), magnetic resonance imaging (MRI), computed tomographic angiography (CTA) and/or the like.

Examples of functional imaging include nuclear perfusion exams such as single photon emission computed tomography (SPECT) or positron emission tomography (PET) and/or the like.

In some advantageous embodiments, the method further comprises receiving information about the patient. The relationship matrix may be provided based on the received information about the patient.

In some variants, the received information indicates at least that the patient belongs to at least one patient group. For example, the information may indicate that the patient belongs to a right-dominant coronary anatomy patient group or a left-dominant coronary anatomy patient group, that the patient belongs to a group having coronary anatomy variants such as coronaries anomalous origin, that the patient belongs to a patient group with prior interventions such as a bypass graft or a stent, that the patient belongs to a group with a known specific prior disease and/or the like.

The relationship matrix may be provided based on the patient belonging to the at least one patient group. In other words, a relationship matrix may be provided that takes into account the received information about the patient and that specifically takes into account that the interrelationships between the first anatomic structures and the second anatomic structures may be different for any of all of the patient groups the patient belongs to.

Providing the relationship matrix may, in some advantageous embodiments, comprise generating a patient-specific relationship matrix based on the received information about the patient and then using the generated patient-specific relationship matrix as the relationship matrix to be used for generating the concordance visualization.

In some advantageous embodiments, providing the relationship matrix comprises receiving the patient-specific relationship matrix, for example from an archiving system of a hospital or other facility or from a data storage medium of the patient themselves.

The patient-specific relationship matrix may be updated, if necessary, with each successive exam of the patient such as to always provide the most accurate information about the interrelatedness (or interrelation) between the first anatomic structures and the second anatomic structures for that specific patient.

In some advantageous embodiments, the concordance visualization comprises a list or table. For example, the table may comprise a column indicating at least one anatomic structure or a group of anatomic structures, a column indicating a result from the first result list of the first type of medical imaging exam, a column indicating results of the second result list of the second type of medical exam and a column indicating a level of concordance between the corresponding first and second result for each of the anatomic structures or group of anatomic structures. This provides an easily graspable and yet complete overview of how the first and second result lists corroborate and/or contradict each other in order to arrive quickly at a decision for a required diagnostic task.

In some advantageous embodiments, the concordance visualization comprises a graphical visualization.

Preferably, the graphical visualization comprises a graphical visualization of the first anatomic structures overlaid with the graphical visualization of the second anatomic structures and/or a graphical visualization of the second anatomic structures overlaid with the graphical visualization of the first anatomic structures. For example, a graphical visualization of a single photon emission computed tomography (SPECT) exam may be realized as a polar plot, sometimes also designated as a bulls-eye-plot. Overlaying the two (or more) graphical visualizations may provide the physician or clinician (or, in general: user of the method and/or system) with an even more intuitively and easily understandable visualization of the first and the second result lists in context with each other.

In some advantageous embodiments, providing the first result list and providing the second result list comprises extracting information from at least one medical exam report using an image processing algorithm and/or a text processing algorithm. The at least one medical exam report may, for example, be a DICOM file, a hand-written or typed report by a physician and/or the like.

In some advantageous embodiments, the first and the second anatomic structures are structures of a mammalian circulatory system, in particular the human circulatory system, preferably of the human heart and connected blood vessels such as coronaries. The invention may, however, also be applied with great benefits to, for example, medical imaging results of a mammalian, in particular human, liver, a mammalian, in particular human, brain and/or the like. In general, the invention is especially advantageous whenever both anatomical imaging exam and a medical imaging exam may be made of a particular region of a body and wherein the two types of imaging exams provide complementary information.

In some advantageous embodiments, generating the concordance visualization comprises determining the respective level of concordance between the at least one of the first anatomic structures and the corresponding first severity indicator on the one hand and the at least one of the second anatomic structures and the corresponding second severity indicator on the other hand.

Determining the level of concordance for one of the first anatomic structures comprises calculating a product of a value based on the first severity indicator for the first anatomic structure with a value from the provided relationship matrix, and calculating a difference metric between the said calculated product and a value based on a second severity indicator of the provided second result list.

Preferably, the second severity indicator used in the difference metric is a second severity indicator for a second anatomic structure that is identical with, part of, or comprises, the first anatomic structure, or is connected to the first anatomic structure by a causal relationship. The difference metric may in a simple case be a simple difference, or an absolute value of a difference.

The value based on the first severity indicator may be the first severity indicator itself or may be a value calculated based on the first severity indicator, in particular when the first severity indicator is a tensor structure such as matrix or a vector itself. Similarly, the value based on the second severity indicator may be a value calculated based on the second severity indicator, in particular when the first severity indicator is a tensor structure such as matrix or a vector itself.

In some advantageous embodiments, at least one threshold value is provided, and the concordance visualization is adapted based on whether the calculated difference metric exceeds the at least one threshold value or not. Preferably, a high level of concordance is determined if the calculated difference metric does not exceed the smallest threshold value of the at least one threshold value (or does not exceed the threshold value in the case that there only is a single threshold value provided).

In other words, the concordance level is determined to be the higher, the closer the determined difference metric is to zero and the lower, the farther the calculated difference metric is from zero. The concordance visualization may indicate different levels of concordance with different visual effects such as different colors, flashing, different acoustic signals and/or the like.

A plurality of threshold values is advantageous when several levels of concordance are to be determined. For example when allowable values for the level of concordance are "low", "medium", "high", than two threshold values may be provided; when the calculated difference metric (preferably an absolute difference) is smaller than the smaller of the two threshold values, the concordance level is predicted to be "high", when the calculated difference metric is between the two provided threshold values, the level of concordance is determined to be "medium", and when the calculated difference metric exceeds the higher of the two provided threshold values, the level of concordance is determined to be "low".

Different levels of concordance may be indicated also as text, for example in a table, or as part of, the concordance visualization, wherein "low", "medium", "high" may be each indicated by a different color in order to immediately make apparent to a user of the method and/or system what levels of concordance have been determined.

In some advantageous embodiments, a first type of medical exam and/or the second type of medical exam comprise any of a computer tomography, a magnetic resonance imaging, an invasive coronary angiography, a nuclear perfusion exam, a computed tomographic angiography (CTA), a single photon emission computer tomography (SPECT) and/or the like.

Although various advantageous options, variants and embodiments have been described in the foregoing with respect to the method according to the first embodiment of the present invention, it should be understood that the same options, variants and embodiments also equally apply to the system according to the second embodiment.

FIG. 1 schematically illustrates a flow diagram for illustrating a computer-implemented method for analyzing medical imaging results according to an embodiment of the first aspect of the present invention.

In a step S100, a first result list of a first type of medical imaging exam of a patient is provided, wherein the first result list indicates a plurality of first anatomic structures and for each of the first anatomic structures a corresponding first severity indicator.

Preferably, the first type of medical imaging exam is an anatomical imaging exam. In the following for the most part an example will be described in which the first result list is a result list of a computed tomography angiography, CTA.

An example for such a first result list from a computed tomography angiography, CTA, is shown in the following Table 1, wherein an 18-segment coronary artery anatomical model is employed. Thus, Table 1 displays a table indicating for each of eighteen (first column) anatomical structures (coronary artery segments, second column) a result with respect to a stenosis diagnosis. A stenosis (or: stricture) is an abnormal narrowing in a blood vessel or other tubular organ or structure.

TABLE 1

| | | Severity of Stenosis | | | | | |
| --- | --- | --- | --- | --- | --- | --- | --- |
| # | anatomical structure | none | minimal | mild | moderate | severe | total occlusion |
| 1 | Proximal RCA | 1 | 0 | 0 | 0 | 0 | 0 |
| 2 | Mid RCA | 0 | 0 | 0 | 1 | 0 | 0 |

TABLE 1-continued

| | | Severity of Stenosis | | | | | |
|---|---|---|---|---|---|---|---|
| # | anatomical structure | none | minimal | mild | moderate | severe | total occlusion |
| 3 | Distal RCA | 1 | 0 | 0 | 0 | 0 | 0 |
| 4 | PDA-R | 1 | 0 | 0 | 0 | 0 | 0 |
| 5 | Left main | 1 | 0 | 0 | 0 | 0 | 0 |
| 6 | Proximal LAD | 0 | 0 | 0 | 1 | 0 | 0 |
| 7 | Mid LAD | 1 | 0 | 0 | 0 | 0 | 0 |
| 8 | Distal LAD | 1 | 0 | 0 | 0 | 0 | 0 |
| 9 | D1 | 1 | 0 | 0 | 0 | 0 | 0 |
| 10 | D2 | 1 | 0 | 0 | 0 | 0 | 0 |
| 11 | Proximal LCs | 1 | 0 | 0 | 0 | 0 | 0 |
| 12 | OM1 | 1 | 0 | 0 | 0 | 0 | 0 |
| 13 | Mid and distal LCx | 0 | 0 | 0 | 0 | 1 | 0 |
| 14 | OM2 | 1 | 0 | 0 | 0 | 0 | 0 |
| 15 | PDA-L | 1 | 0 | 0 | 0 | 0 | 0 |
| 16 | PLB-R | 1 | 0 | 0 | 0 | 0 | 0 |
| 17 | Ramus intermedius | 1 | 0 | 0 | 0 | 0 | 0 |
| 18 | PLB-L | 1 | 0 | 0 | 0 | 0 | 0 |

In Table 1, "LAD" indicates the left anterior descending coronary artery, "PDA-L" indicates the left posterior descending artery, "PLB-L" indicates the left posterolateral branch, "RCA" indicates the right main coronary artery, "PDA-R" indicates the right posterior descending artery, and "PLB-R" indicates the right posterolateral branch, see also Gilbert L. Raff et al.

Figure 2:
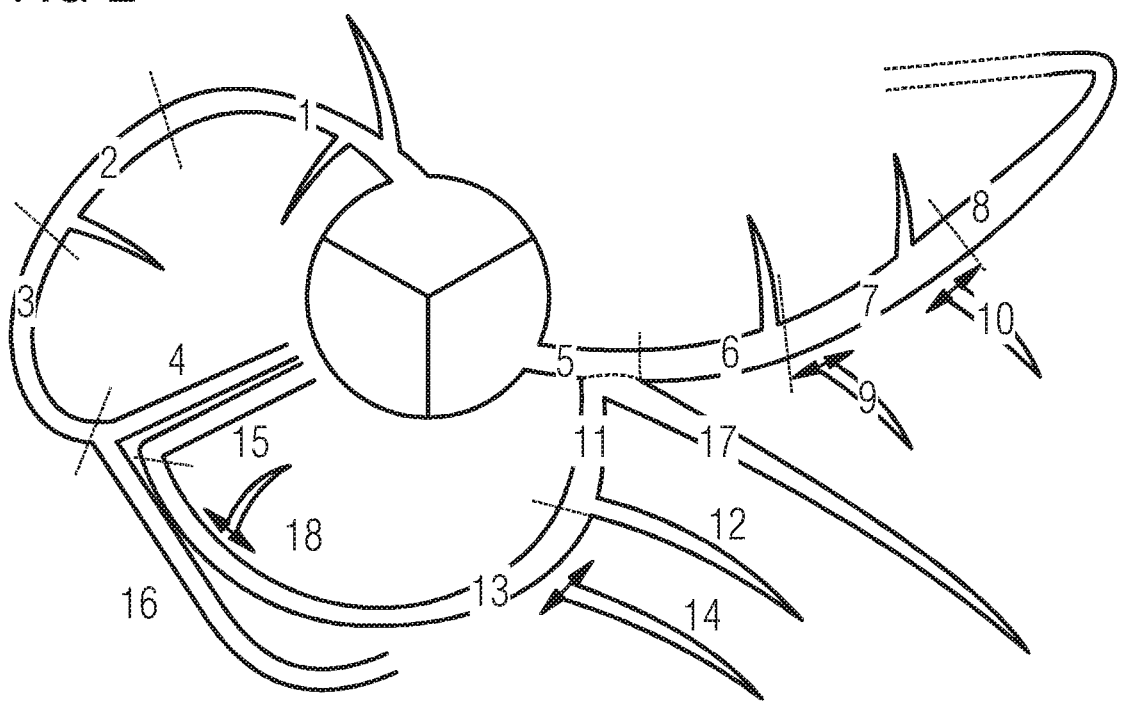
FIG. 2 shows a schematic diagram of a coronary segmentation.

FIG. 2 show a schematic diagram of a coronary segmentation according to the Society of Cardiovascular Computed Tomography (SCCT), see e.g. Raff et al.

The third to eight columns of Table 1 comprise severity indication information which indicates, for each anatomical structure, a severity level of the stenosis in that anatomical structure as resulting from the performed test. The severity indication information, i.e. the plurality of severity labels, may be one type of a severity indicator.

The severity labels may range, in the order of lowest to highest, from "none", over "minimal", "mild", "moderate", and "severe" up to "total occlusion". Definitions for these severity labels may be made as follows (see e.g. Raff et al.):

| | |
|---|---|
| "none" | absence of plaque; no luminal stenosis |
| "minimal" | plaque with less than 25% stenosis |
| "mild" | 25% to 49% stenosis |
| "moderate" | 50% to 69% of stenosis |
| "severe" | 70% to 99% stenosis |
| "total occlusion" | 100% stenosis |

Table 1 is designed such that each line will comprise one and only one entry of "1" which indicates that the severity level according to the column in which the "1" is situated has been found by the exam. Thus, for example, Table 1 indicates that, in the described exam, the anatomical region #2, i.e. the middle region of the right coronary artery ("Mid RCA"), has been found to show moderate stenosis (i.e. a stenosis of moderate severity level).

Providing the first result list in step S100 may comprise generating, in a step S150, an updated result list in which a single value as a severity indicator is provided for each of the first anatomical regions #1 to #18.

For example, continuing the example from the above Table 1, a severity vector may be defined which assigns a numeric value to each severity label and creates a single numeric value from the severity indication information as shown in Table 1.

For example, the severity vector for the first result list may be defined as $[0, 1, 2, 3, 4, 5]^T/\Sigma(0, 1, 2, 3, 4, 5)$, i.e. a normalized column vector (small upper "T" here indicating the transposition operation). In other words, the severity vector may be defined as $[0, 1/15, 2/15, 3/15, 4/15, 5/15]^T$ or, in expressed yet differently, as $[0, 1/15, 2/15, 1/5, 4/15, 1/3]^T$.

An updated result list may then be generated from the result list shown in Table 1 by matrix-multiplying, for each of the first anatomical regions (#1 to #18), the entries in columns three to eight with the severity vector such that a single scalar value as a severity indicator is left over.

In formulae, when the originally provided result list of the anatomical exam is designated as FM_CTA (i.e. CTA findings matrix for computed tomographic angiography, CTA, represented by the third to eighth column of Table 1), and the severity vector is designated as NORMALIZED_CTA_SEVERITY_SCALE, and the updated result list is designated as UPDATED_FM_CTA, then UPDATED_FM_CTA=FM_CTA*NORMALIZED_CTA_SEVERITY_SCALE, wherein the "*" marks the line-wise multiplication; in this way, from the 18×6 matrix (18 anatomical regions times 6 severity labels) FM_CTA and the 6×1 severity vector NORMALIZED_CTA_SEVERITY_SCALE, the 18×1 matrix UPDATED_FM_CTA is generated.

Such an updated result list UPDATED_FM_CTA using the result list in Table 1 and the above severity vector NORMALIZED_CTA_SEVERITY_SCALE is shown in the following Table 2:

TABLE 2

| # | anatomical structure | Severity |
|---|---|---|
| 1 | Proximal RCA | 0 |
| 2 | Mid RCA | 1/5 |
| 3 | Distal RCA | 0 |
| 4 | PDA-R | 0 |
| 5 | Left main | 0 |
| 6 | Proximal LAD | 1/5 |
| 7 | Mid LAD | 0 |
| 8 | Distal LAD | 0 |
| 9 | D1 | 0 |
| 10 | D2 | 0 |
| 11 | Proximal LCs | 0 |
| 12 | OM1 | 0 |
| 13 | Mid and distal LCx | 4/15 |
| 14 | OM2 | 0 |
| 15 | PDA-L | 0 |
| 16 | PLB-R | 0 |
| 17 | Ramus intermedius | 0 |
| 18 | PLB-L | 0 |

This updated result list may then be used as the first result list provided in step S100; it has the advantage that some calculations are simplified by having a single numeric value (e.g. 4/15) as the severity indicator.

The updated result list (or: updated findings matrix) may also be designated as a result vector as it can be written as a 18×1 matrix (i.e. a vector) in which each line corresponds to one of the eighteen coronary artery segments.

Referring back to FIG. 1, in a second step S200, a second result list of a second type of medical imaging exam of the patient is provided, wherein the second result list indicates a plurality of second anatomic structures and for each of the second anatomic structures a corresponding second severity indicator.

Preferably, the second type of medical imaging exam is a functional imaging exam. In the following for the most part an example will be described in which the second result list is a result list of a single photon emission computed tomography, SPECT.

An example for such a second result list from a single photon emission computed tomography, SPECT, for the left ventricle (LV) is shown in the following Table 3. Table 3 displays a table indicating for each of seventeen (first column, from #1 to #17) anatomical structures (myocardial perfusion territories, second column) a result with respect to a perfusion deficit diagnosis (third to sixth column). Thus, the numbers in the third to sixth column represent a SPECT findings matrix, FM_SPECT.

TABLE 3

| | | Severity of Perfusion Deficit | | | |
|---|---|---|---|---|---|
| # | | none | mild | moderate | severe |
| 1 | basal anterior | 0 | 1 | 0 | 0 |
| 2 | basal anteroseptal | 1 | 0 | 0 | 0 |
| 3 | basal inferoseptal | 1 | 0 | 0 | 0 |
| 4 | basal inferior | 0 | 0 | 1 | 0 |
| 5 | basal inferolateral | 0 | 0 | 1 | 0 |
| 6 | basal anterolateral | 1 | 0 | 0 | 0 |
| 7 | mid anterior | 1 | 0 | 0 | 0 |
| 8 | mid anteroseptal | 0 | 1 | 0 | 0 |
| 9 | mid inferoseptal | 1 | 0 | 0 | 0 |
| 10 | mid inferior | 1 | 0 | 0 | 0 |
| 11 | mid inferolateral | 1 | 0 | 0 | 0 |
| 12 | mid anterolateral | 1 | 0 | 0 | 0 |
| 13 | apical anterior | 1 | 0 | 0 | 0 |
| 14 | apical septal | 1 | 0 | 0 | 0 |
| 15 | apical inferior | 1 | 0 | 0 | 0 |
| 16 | apical lateral | 1 | 0 | 0 | 0 |
| 17 | apex | | | | |

The severity labels used for the SPECT findings matrix FM_SPECT may range, in the order of lowest to highest, from "none", over "mild" and "moderate" to "severe".

Again, the plurality of severity labels in the SPECT findings matrix FM_SPECT represent a kind of severity indicator.

More advantageously, however, similarly as in the case of the CTA findings matrix FM_CTA, an updated SPECT findings matrix UPDATED_FM_SPECT may be generated in a step S250 which may be provided as the second result list in step S200. In other words, providing the second result list in step S200 may comprise generating, in a step S250, an updated result list in which a single value as a severity indicator is provided for each of the second anatomical regions #1 to #17.

Again, for this task a severity vector NORMALIZED_SPECT_SEVERITY_SCALE may be defined. For example, the severity vector for the second result list may be defined as $[0, 1, 2, 3]^T/\Sigma(0, 1, 2, 3)$, i.e. a normalized column vector (small upper "T" here indicating the transposition operation). In other words, the severity vector may be defined as $[0, 1/6, 2/6, 3/6]^T$ or, in expressed yet differently, as $[0, 1/6, 1/3, 1/2]^T$.

In formulae, when the originally provided result list of the functional perfusion exam is designated as FM_SPECT (i.e. findings matrix for a single photon emission computed tomography, SPECT, represented by the third to sixth column of Table 3), and the severity vector is designated as NORMALIZED_SPECT_SEVERITY_SCALE, and the updated result list is designated as UPDATED_FM_SPECT, then:

UPDATED_FM_SPECT=FM_SPECT*NORMALIZED_SPECT_SEVERITY_SCALE, wherein the "*" marks the line-wise multiplication; in this way, from the 17×4 matrix (18 anatomical regions times 4 severity labels) FM_SPECT and the 4×1 severity vector NORMALIZED_SPECT_SEVERITY_SCALE, the 17×1 matrix UPDATED_FM_SPECT is generated.

Generally speaking, a severity vector for a findings matrix FM_X for a type X of exam (or a modality X) may be given by $[0, 1, 2, 3, \ldots, N_x]^T/\Sigma(0, 1, 2, 3, \ldots N_x)$, $N_x$ being the total number of severity labels used for the type X of exam. In the present examples, $N_{CTA}=6$ for X=CTA and $N_{SPECT}=4$ for X=SPECT.

Such an updated result list UPDATED_FM_SPECT (or: updated findings matrix) using the result list (or findings matrix FM_SPECT) in Table 3 and the above severity vector NORMALIZED_SPECT_SEVERITY_SCALE is shown in the following Table 4:

TABLE 4

| # | | severity |
|---|---|---|
| 1 | basal anterior | 1/6 |
| 2 | basal anteroseptal | 0 |
| 3 | basal inferoseptal | 0 |
| 4 | basal inferior | 1/3 |
| 5 | basal inferolateral | 1/3 |
| 6 | basal anterolateral | 0 |
| 7 | mid anterior | 0 |
| 8 | mid anteroseptal | 1/6 |
| 9 | mid inferoseptal | 0 |
| 10 | mid inferior | 0 |
| 11 | mid inferolateral | 0 |
| 12 | mid anterolateral | 0 |
| 13 | apical anterior | 0 |
| 14 | apical septal | 0 |
| 15 | apical inferior | 0 |
| 16 | apical lateral | 0 |
| 17 | apex | 0 |

The updated result list or updated findings matrix may also be designated as a result vector as it can be written as a 17×1 matrix (i.e. a vector) in which each line corresponds to one of the seventeen myocardial perfusion territories.

Figure 3:
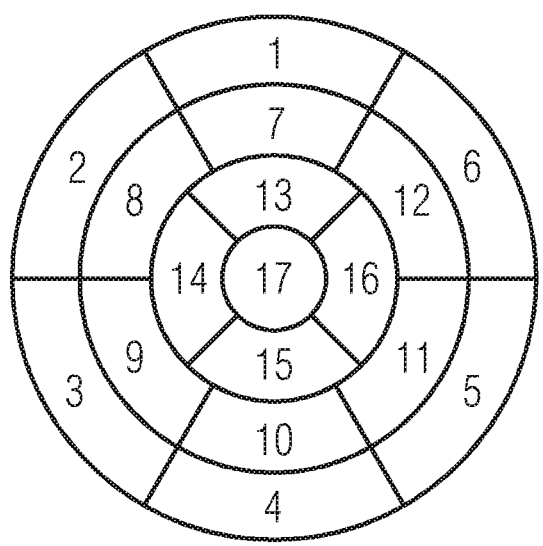
FIG. 3 a Bulls-eye plot for indicating perfusion deficits as found in a myocardial perfusion imaging exam of the left ventricle of the human heart.

Results of myocardial perfusion exams in particular for the left ventricle separated into the above 17 myocardial perfusion territories, or segments ("17-segment model") may be portrayed in so-called Bulls-eye plots (or polar plots) as shown in FIG. 3. In Bulls-eye plots, higher perfusion deficits are usually marked by stronger colors ranging from yellow (low deficit) to red (high deficit). In FIG. 3, the Bulls-eye plot is shown as indicating no perfusion deficits.

For example the American Heart Association (AHA) Writing Group on Myocardial Segmentation and Registration for Cardiac Imaging recommends the 17-segment model of the left ventricle as an optimally weighted approach for the visual interpretation of regional left ventricular (LV) abnormalities by multiple cardiac imaging techniques.

In a step S300, a relationship matrix indicating a level of interrelatedness between the first anatomic structures and the second anatomic structures is provided.

As has been described in the foregoing, the relationship matrix may be a general relationship matrix (used for all patients alike).

The relationship matrix may also be a patient-group-specific relationship matrix, in which case step S300 may comprise a step S350 of receiving information about the patient, said information e.g. indicating at least that the patient belongs to at least one patient group. For example, the information may indicate that the patient belongs to a right-dominant coronary anatomy patient group or a left-dominant coronary anatomy patient group, that the patient belongs to a group having coronary anatomy variants such as coronaries anomalous origin, that the patient belongs to a patient group with prior interventions such as a bypass graft or a stent, that the patient belongs to a group with a known specific prior disease and/or the like.

The relationship matrix may also be a patient-specific relationship matrix in which prior knowledge of the inter-relation (or interrelatedness) of specific of the first anatomical structures with specific of the second anatomical structures for one specific patient. Said prior knowledge may stem from the prior medical history of the patient and may be automatically extracted, e.g. by machine learning, preferably by a trained artificial neural network.

In the following, in Tables 5A, 5B and 5C an example relationship matrix is depicted which comprises indicators of interrelatedness (or, expressed differently, weights of association) between the eighteen coronary artery segments (lines) according to the 18-segment model and the seventeen myocardial perfusion territories (columns) according to the 17-segment model.

In Tables 5A, 5B and 5C in reality each entry will be filled by a number. For the present example, only a few example entries have been filled whereas other blocks have been filled with a placeholder "..".

TABLE 5A

|  | 1 basal anterior | 2 basal antero-septal | 3 basal infero-septal | 4 basal inferior | 5 basal infero-lateral | 6 basal antero-lateral |
|---|---|---|---|---|---|---|
| 1 Proximal RCA | 1 | 2 | 3 | 3 | ... | ... |
| 2 Mid RCA | 1 | 2 | 3 | 3 | ... | ... |
| 3 Distal RCA | 1 | 2 | 3 | 3 | ... | ... |
| 4 PDA-R | 1 | 2 | 3 | 3 | ... | ... |
| 5 Left main | 1 | 2 | 3 | 3 | ... | ... |
| 6 Proximal LAD | 3 | 3 | 2 | — | ... | ... |
| 7 Mid LAD | 3 | 3 | 2 | — | ... | ... |
| 8 Distal LAD | 3 | 3 | 2 | — | ... | ... |
| 9 D1 | 3 | 3 | 2 |  | ... | ... |
| 10 D2 | 3 | 3 | 2 |  | ... | ... |
| 11 Proximal LCs | 2 | 1 | ... | ... | 3 | 3 |
| 12 OM1 | 2 | 1 | ... | ... | 3 | 3 |
| 13 Mid and distal LCx | 2 | 1 | ... | ... | 3 | 3 |
| 14 OM2 | 2 | 1 | ... | ... | 3 | 3 |
| 15 PDA-L | 2 | 1 | ... | ... | 3 | 3 |
| 16 PLB-R | ... | ... | ... | ... | ... | ... |
| 17 Ramus intermedius | ... | ... | ... | ... | ... | ... |
| 18 PLB-L | ... | ... | ... | ... | ... | ... |

TABLE 5B

|  | 7 mid anterior | 8 mid antero-septal | 9 mid infero-septal | 10 mid inferior | 11 mid infero-lateral | 12 mid antero-lateral |
|---|---|---|---|---|---|---|
| 1 Proximal RCA | ... | 2 | 3 | 3 | ... | ... |
| 2 Mid RCA | ... | 2 | 3 | 3 | ... | ... |
| 3 Distal RCA | ... | 2 | 3 | 3 | ... | ... |
| 4 PDA-R | ... | 2 | 3 | 3 | ... | ... |
| 5 Left main | ... | 2 | ... | ... | ... | ... |
| 6 Proximal LAD | 3 | 3 | 2 | ... | ... | ... |
| 7 Mid LAD | 3 | 3 | 2 | ... | ... | ... |
| 8 Distal LAD | 3 | 3 | 2 | ... | ... | ... |
| 9 D1 | 3 | 3 | 2 | ... | ... | ... |
| 10 D2 | 3 | 3 | 2 | ... | ... | ... |
| 11 Proximal LCs | ... | ... | ... | ... | 3 | 3 |
| 12 OM1 | ... | ... | ... | ... | 3 | 3 |
| 13 Mid and distal LCx | ... | ... | ... | ... | 3 | 3 |
| 14 OM2 | ... | ... | ... | ... | 3 | 3 |
| 15 PDA-L | ... | ... | ... | ... | 3 | 3 |
| 16 PLB-R | ... | ... | ... | ... | ... | ... |
| 17 Ramus intermedius | ... | ... | ... | ... | ... | ... |
| 18 PLB-L | ... | ... | ... | ... | ... | ... |

TABLE 5C

|   |                  | 13 apical anterior | 14 apical septal | 15 apical inferior | 16 apical lateral | 17 apex |
|---|------------------|--------------------|------------------|--------------------|-------------------|---------|
| 1 | Proximal RCA     | ...                | ...              | 3                  | ...               | ...     |
| 2 | Mid RCA          | ...                | ...              | 3                  | ...               | ...     |
| 3 | Distal RCA       | ...                | ...              | 3                  | ...               | ...     |
| 4 | PDA-R            | ...                | ...              | 3                  | ...               | ...     |
| 5 | Left main        | ...                | ...              | ...                | ...               | ...     |
| 6 | Proximal LAD     | 3                  | 3                | ...                | ...               | 3       |
| 7 | Mid LAD          | 3                  | 3                | ...                | ...               | 3       |
| 8 | Distal LAD       | 3                  | 3                | ...                | ...               | 3       |
| 9 | D1               | 3                  | 3                | ...                | ...               | 3       |
| 10| D2               | 3                  | 3                | ...                | ...               | 3       |
| 11| Proximal LCs     | ...                | ...              | ...                | 3                 | ...     |
| 12| OM1              | ...                | ...              | ...                | 3                 | ...     |
| 13| Mid and distal LCx | ...              | ...              | ...                | 3                 | ...     |
| 14| OM2              | ...                | ...              | ...                | 3                 | ...     |
| 15| PDA-L            | ...                | ...              | ...                | 3                 | ...     |
| 16| PLB-R            | ...                | ...              | ...                | ...               | ...     |
| 17| Ramus intermedius| ...                | ...              | ...                | ...               | ...     |
| 18| PLB-L            | ...                | ...              | ...                | ...               | ...     |

From Table 5C it is evident, for example, that the Proximal RCA coronary artery segment is strongly (value of 3) interrelated with the apical inferior myocardial perfusion territory.

Preferably, the relationship matrix is not just specific to anatomic regions but also to the exams for which the segmentation into the first and second anatomical regions, respectively, is provided. For example, the relationship matrix illustrated in Tables 5A, 5B and 5C is a relationship matrix indicating an interrelation between the coronary artery segments of the computed tomographic angiography, CTA with the myocardial perfusion territories of a single photon emission computed tomography, SPECT.

Said relationship matrix may thus be designated as $RM_{SPECT\rightarrow CTA}$ (an 18×17 matrix). The relationship matrix indicating the interrelation the other way round, i.e. $RM_{CTA\rightarrow SPECT}$, is simply the transpose of $RM_{SPECT\rightarrow CTA}$, i.e. $RM^T_{SPECT\rightarrow CTA}$ (a 17×18 matrix)

Preferably, the relationship matrix is provided as a column-wise normalized relationship matrix $NORM\_RM_{SPECT\rightarrow CTA}$, calculated according to the following entry-wise definition, wherein "M(i,j)" indicates the entry in the i-th line and the j-th column of a matrix M:

$NORM\_RM_{SPECT\rightarrow CTA}(i,j) = RM_{SPECT\rightarrow CTA}(i,j)/\Sigma\_i(RM_{SPECT\rightarrow CTA}(i,j))$, wherein $\Sigma$ again designates a sum, and $\Sigma\_i$ the sum over lines i (with fixed column j).

Compared to the non-normalized relationship matrix $RM_{SPECT\rightarrow CTA}$ the normalized relationship matrix $NORM\_RM_{SPECT\rightarrow CTA}$ has the advantage that the contribution from each of the first anatomic structures (in the present example, of each coronary artery segment from the computed tomographic angiography, CTA) is spread over all of the second anatomic structures (in the present example, all myocardial perfusion territories from the single photon emission computed tomography, SPECT) and vice versa.

In a step S400, based on the provided first result list, the provided second result list and the provided relationship matrix, a concordance visualization is generated which indicates a respective level of concordance between at least one of the first anatomic structures and the corresponding first severity indicator on the one hand, and at least one of the second anatomic structures and the corresponding second severity indicator on the other hand.

Preferably, the concordance visualization indicates the respective level of concordance between each and all of the first anatomic structures and each and all of the second anatomic structures, or the respective level of concordance between at least those first anatomic structures and second anatomic structures for which a severity label higher than the lowest severity label has been determined.

One example for such a concordance visualization is given by Table 6 which shows a concordance visualization in form of a table:

TABLE 6

|                       | CTA                    | SPECT                                         | Determined Concordance Level |
|-----------------------|------------------------|-----------------------------------------------|------------------------------|
| Left Main             | No significant stenosis| None                                          | High                         |
| Left Anterior         | Moderate stenosis      | Reversible perfusion defect (moderate)        | Medium                       |
| Left Circumflex       | Severe stenosis        | Reversible perfusion defect (moderate-severe) | High                         |
| Right Coronary Artery | Moderate stenosis      | Reversible perfusion defect (moderate-severe) | High                         |

The first column in Table 6 comprises groups of anatomic structures, for example, the "Left Circumflex" group of Table 6 comprises first anatomic structures (i.e. coronary artery segments) #11 to #15 according to the 18-segment model.

The concordance levels may be determined for example in the following way:

A difference vector $\Delta V\_SPECT$ is calculated between the matrix product of the updated findings matrix UPDATED_FM_CTA for the first type of medical imaging exam (here: CTA) and the normalized relationship matrix $NORM\_RM_{CTA\rightarrow SPECT}$ and the updated findings matrix UPDATED_FM_SPECT for the second type of medical imaging exam (here: SPECT).

In formulae:

$\Delta V\_SPECT = (UPDATED\_FM\_CTA * NORM\_RM_{CTA\rightarrow SPECT}) - UPDATED\_FM\_SPECT$, such that a 17-line difference vector is generated (by subtracting the 17×1 structure UPDATED_FM_SPECT from a 17×1 structure resulting from a matrix multiplication ("*") between the 18×1 structure UPDATED_FM_CTA and the 18×17 structure $NORM\_RM_{CTA\rightarrow SPECT}$).

Said difference vector $\Delta V\_SPECT$ now describes for all of the seventeen myocardial perfusion territories of the second type of exam (here: SPECT) a level of concordance with the findings of the first type of medical imaging exam (here: CTA).

As has been described, a number of threshold values may be defined based on which the concordance visualization is adapted, e.g. showing a "High" level of concordance when the corresponding entry in the difference vector $\Delta V\_SPECT$ is between zero and a first threshold value TV1, showing a "Medium" level of concordance when the corresponding entry in the difference vector $\Delta V\_SPECT$ is between the first threshold value TV1 and a second threshold value TV2, and showing a "High" level of concordance when the corresponding entry in the difference vector $\Delta V\_SPECT$ is larger than the second threshold value TV2. The threshold values may be adapted for each application of the present method.

In analogy to the above, a difference vector ΔV_CTA may be calculated by:

$$\Delta V\_CTA = (UPDATED\_FM\_SPECT * NORM\_RM_{SPECT \to CTA}) - UPDATED\_FM\_CTA.$$

The concordance levels may be based on any or both of the corresponding entries of the difference vector ΔV_CTA and the difference vector ΔV_SPECT.

Optionally, the different determined concordance levels may be marked by different colors, e.g. High=green, Medium=yellow and Low=red.

In some advantageous embodiments, a user may be provided with a graphical visualization of the results of the first type of medical imaging exam as well as with a graphical visualization of the results of the second type of medical imaging exam side by side, e.g. by one of the plots shown in FIG. 2 or FIG. 3 each. The user may then select one of the anatomic regions (first or second, respectively) in the graphical visualization. Automatically, in the respective other graphical visualization at least one anatomical region may be visually indicated or highlighted for which a predetermined level of concordance (e.g. "Medium" or above; or only "High") has been determined.

For example, when a user clicks on, or selects, a stenosis findings from a CTA exam, report, pictogram or plot, relevant myocardial perfusion territories on a SPECT exam, report, pictogram or plot are automatically indicated or highlighted.

The concordance visualization itself may be a graphical visualization. Apart from a side-by-side comparison as has been described, graphical visualizations of each of the two types of medical imaging exams may be overlaid.

FIG. 4, for example, shows a side-by-side overview of findings from a functional exam (here: SPECT, on the left) and an anatomical exam (here: CTA, on the right), wherein areas of higher severity are marked as darker.

Figure 5:
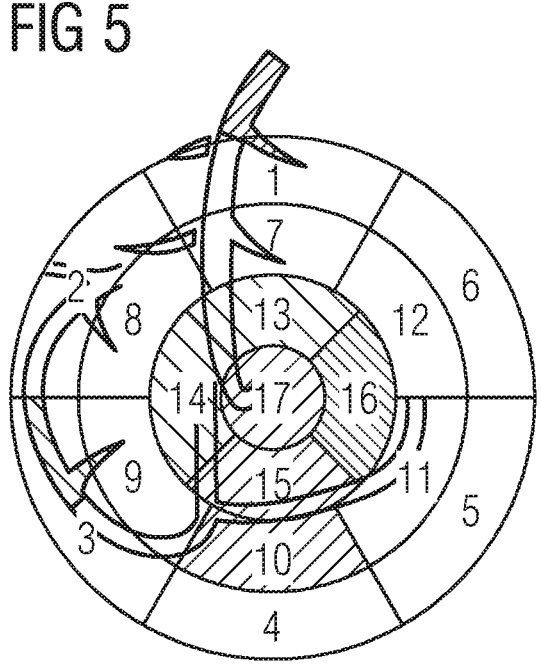
FIG. 5 shows another possible type of graphical concordance visualization.

FIG. 5, for example, shows coronaries with annotated stenosis results overlaid on a Bulls-eye plot.

Figure 6:
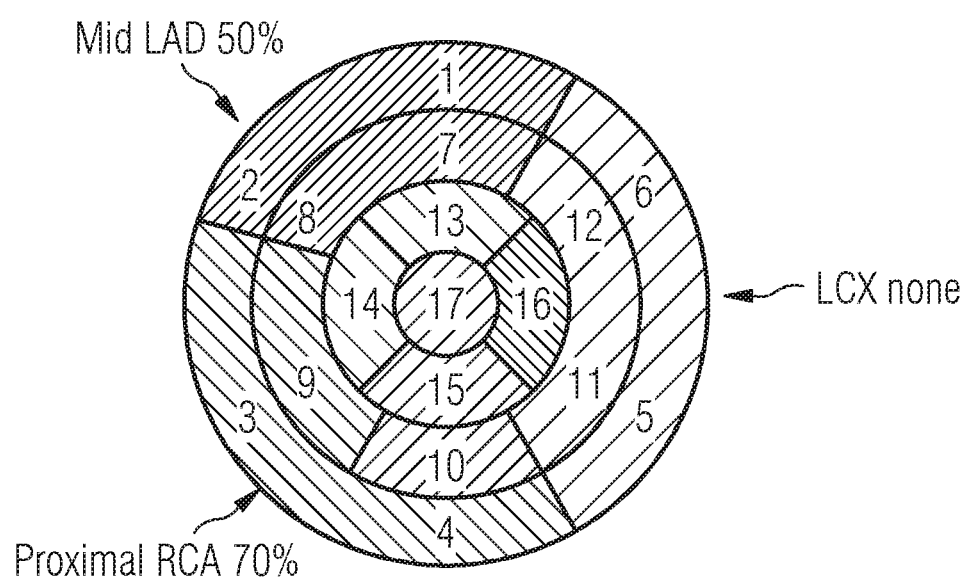
FIG. 6 shows yet another possible type of graphical concordance visualization.

FIG. 6, for example, shows overlaid territories on a Bulls-eye plot with corresponding stenosis information.

FIG. 7 shows a schematic block diagram illustrating a system 100 for analyzing medical results according to an embodiment of the second aspect of the present invention. The system 100 comprises a computing device 110 configured to perform the method according to an embodiment of the first aspect of the present invention, in particular to one of the variants described in the foregoing with respect to FIG. 1 to FIG. 6, and optionally a display device 120 configured to display the generated concordance visualization, e.g. in one of the ways as has been described in the foregoing with respect to FIG. 4 to FIG. 6.

The computing device 110 may comprise a central processing unit (CPU) 112 and a memory 113 operatively connected to the CPU 112. The computing device comprises an output interface 114 for outputting signals, for example to the display device 120, and an input interface 111 for receiving data, for example result lists of medical imaging exams and/or information about patients as has been described in the foregoing in particular with respect to steps S100, S200 and S300.

The computing device 110 may be partially, or completely, realized as a remote device such as a server, in particular as a cloud computing device realized on a cloud computing platform.

The display 120 device may be a monitor, a computer screen, a touch screen, a holographic screen, a virtual reality display, an augmented reality display, a mixed reality display and/or the like.

FIG. 8 shows a schematic block diagram illustrating a computer program product 200 according to the third embodiment of the present invention. The computer program product 200 comprises executable program code 250 configured to, when executed by a processor, perform the method according to an embodiment of the first aspect of the present invention, in particular as has been described with respect to FIG. 1 to FIG. 6 in the foregoing.

FIG. 8 shows a schematic block diagram illustrating a non-transitory computer-readable data storage medium 300 according to the fourth embodiment of the present invention. The data storage medium 300 comprises executable program code 350 configured to, when executed by a processor, perform the method according to an embodiment of the first aspect of the present invention, in particular as has been described with respect to FIG. 1 to FIG. 6 in the foregoing.

The embodiments have been chosen and described in order to best explain the principles of the invention and its practical applications, to thereby enable others skilled in the art to best utilize the invention and various embodiments with various modifications as are suited to the particular use contemplated.

Although the embodiments described in detail refer to medical imaging of the human heart, other parts of the mammalian, in particular human, body may be examined.

Another application of the present invention is, for example, in the field of liver imaging exams, e.g. of trans-arterial chemo-embolization (TACE) of a tumor within the liver.

The liver is generally divided into eight segments, wherein segment 4 has a 4a and 4b part. These segments are fed with arterial supply from branches of the hepatic artery. By a result list of an anatomical imaging exam (as the first type of medical imaging exam) it may be made clear in which segment a tumor resides, for example in segment 6. The first type of medical imaging exam in this case may be a computed tomography, CT, exam.

A functional imaging exam as the second type of imaging exam (for example perfusion ultrasound using contrast medium) may show that the inferior hepatic branch is feeding the tumor area within segment 6 so that this artery branch would be the target artery where the trans-arterial chemo-embolization TACE can be performed. This, again, would be indicated by high levels of concordance determined between segment 6 (as one of the first anatomic structures) and the inferior hepatic branch (as one of the second anatomic structures).

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for analyzing medical imaging results, comprising:
   providing a first result list of a first type of medical imaging exam of a patient, the first result list indicating a plurality of first anatomic structures and indicating, for each respective first anatomic structure of the plurality of first anatomic structures, a corresponding first severity indicator;
   providing a second result list of a second type of medical imaging exam of the patient, the second result list indicates a plurality of second anatomic structures and indicating, for each respective second anatomic structure of the plurality of the second anatomic structures, a corresponding second severity indicator;
   providing a relationship matrix indicating a level of interrelatedness between the first anatomic structures and the second anatomic structures; and
   generating, based on the first result list provided, on the second result list and on the relationship matrix provided, a concordance visualization indicating a respective level of concordance between at least one of the first anatomic structures and the corresponding first severity indicator, and indicating a respective level of concordance between at least one of the second anatomic structures and the corresponding second severity indicator.

2. The method of claim 1, wherein the first type of medical imaging exam is an anatomical imaging exam and the second type of medical imaging exam is a functional imaging exam.

3. The method of claim 1, further comprising:
   receiving information about the patient, wherein the relationship matrix is provided based on the information received about the patient.

4. The method of claim 3, wherein the information received indicates at least that the patient belongs to at least one patient group; and wherein the relationship matrix is provided based on the patient belonging to the at least one patient group.

5. The method of claim 3, further comprising:
   generating a patient-specific relationship matrix based on the information received about the patient; and
   providing the patient-specific relationship matrix generated as the relationship matrix.

6. The method of claim 1, wherein the providing of the relationship matrix includes receiving a patient-specific relationship matrix.

7. The method of claim 1, wherein the concordance visualization includes a list or table.

8. The method of claim 1, wherein the concordance visualization includes a graphical visualization.

9. The method of claim 8, wherein the concordance visualization includes a graphical visualization of the first anatomic structures overlaid with a graphical visualization of the second anatomic structures or a graphical visualization of the second anatomic structures overlaid with a graphical visualization of the first anatomic structures.

10. The method of claim 1, wherein at least one of the providing of the first result list and the providing of the second result list includes extracting information from at least one medical exam report using at least one of an image processing algorithm and a text processing algorithm.

11. The method of claim 1, wherein the first anatomic structures and the second anatomic structures are structures of a human circulatory system.

12. The method of claim 11, wherein the first anatomic structures and the second anatomic structures are structures of a human heart.

13. The method of claim 1, wherein the generating of the concordance visualization includes determining the respective level of concordance; and wherein the determining of the level of concordance for one of the first anatomic structures includes
   calculating a product of a value based on the first severity indicator for the first anatomic structure with a value from the provided relationship matrix, and
   calculating a difference metric between the product calculated and a value based on a second severity indicator of the provided second result list.

14. The method of claim 13, wherein at least one threshold value is provided; and wherein the concordance visualization is adapted based on whether or not the difference metric calculated exceeds the at least one threshold value.

15. The method of claim 14, wherein a relatively high level of concordance is determined upon the difference metric calculated not exceeding a relatively smallest threshold value of the at least one threshold value.

16. A non-transitory computer program product storing executable program code configured to, when executed by at least one processor, perform the method of claim 1.

17. A system for analyzing medical results, comprising:
   at least one processor configured to
      provide a first result list of a first type of medical imaging exam of a patient, the first result list indicating a plurality of first anatomic structures and indicating, for each respective first anatomic structure of the plurality of first anatomic structures, a corresponding first severity indicator,
      provide a second result list of a second type of medical imaging exam of the patient, the second result list indicates a plurality of second anatomic structures and indicating, for each respective second anatomic structure of the plurality of the second anatomic structures, a corresponding second severity indicator,
      provide a relationship matrix indicating a level of interrelatedness between the first anatomic structures and the second anatomic structures, and
      generate, based on the first result list provided, on the second result list and on the relationship matrix provided, a concordance visualization indicating a respective level of concordance between at least one of the first anatomic structures and the corresponding first severity indicator, and indicating a respective level of concordance between at least one of the second anatomic structures and the corresponding second severity indicator; and a display device configured to display the concordance visualization generated.

18. The system of claim 17, wherein the first type of medical imaging exam is an anatomical imaging exam and the second type of medical imaging exam is a functional imaging exam.

19. The system of claim 17, wherein the at least one processor is further configured to receive information about the patient, wherein the relationship matrix is provided based on the information received about the patient.

20. A non-transitory computer-readable data storage medium storing executable program code configured to, when executed by at least one processor, perform a method for analyzing medical imaging results, comprising:

providing a first result list of a first type of medical imaging exam of a patient, the first result list indicating a plurality of first anatomic structures and indicating, for each respective first anatomic structure of the plurality of first anatomic structures, a corresponding first severity indicator;

providing a second result list of a second type of medical imaging exam of the patient, the second result list indicates a plurality of second anatomic structures and indicating, for each respective second anatomic structure of the plurality of the second anatomic structures, a corresponding second severity indicator;

providing a relationship matrix indicating a level of interrelatedness between the first anatomic structures and the second anatomic structures; and generating, based on the first result list provided, on the second result list and on the relationship matrix provided, a concordance visualization indicating a respective level of concordance between at least one of the first anatomic structures and the corresponding first severity indicator, and indicating a respective level of concordance between at least one of the second anatomic structures and the corresponding second severity indicator.

* * * * *